United States Patent [19]
Haber

[11] 3,984,298
[45] Oct. 5, 1976

[54] ELECTROMOLECULAR PROPULSION IN SEMICONDUCTIVE MEDIA

[75] Inventor: Norman Haber, Old Tappan, N.J.

[73] Assignee: Haber Instruments, Incorporated, Palisades Park, N.J.

[22] Filed: Dec. 28, 1970

[21] Appl. No.: 102,120

[52] U.S. Cl. .................... 204/180 S; 204/180 R; 204/186
[51] Int. Cl.$^2$ ......................... B01K 5/00
[58] Field of Search ............ 204/180 R, 180 S, 186, 204/190, 299

[56] References Cited

UNITED STATES PATENTS

| | | | |
|---|---|---|---|
| 1,529,348 | 3/1925 | Eddy | 204/190 |
| 1,886,236 | 11/1932 | Meissner | 317/258 |
| 2,944,952 | 7/1960 | McMinn, Jr. | 204/186 X |
| 2,947,677 | 8/1960 | Buckwedel | 204/181 |
| 2,982,707 | 5/1961 | Scheible | 204/181 |
| 3,042,597 | 7/1962 | Schumacher | 204/180 R |
| 3,133,009 | 5/1964 | Natelson | 204/180 S |
| 3,317,417 | 5/1967 | Raymond | 204/299 |
| 3,384,566 | 5/1968 | Clark | 204/181 |
| 3,437,575 | 4/1969 | Gross et al. | 204/186 |
| 3,437,597 | 4/1969 | Belloc | 252/62.9 |
| 3,468,778 | 9/1969 | Hirs et al. | 204/180 |
| 3,511,651 | 5/1970 | Rosenberg | 204/180 R X |
| 3,535,602 | 10/1970 | Hrach et al. | 317/258 |
| 3,542,608 | 11/1970 | Jensen et al. | 148/186 |

OTHER PUBLICATIONS

Cawley, "Electrophoresis and Immunoelectrophoresis", Little, Brown Co., (1969), pp. 5 & 6.

*Primary Examiner*—John H. Mack
*Assistant Examiner*—A. C. Prescott

[57] ABSTRACT

This application is directed to a high-voltage electromotive process to excite a chemical species, which includes orientating, re-positioning and transporting and for the separation of chemical species on a support. Unlike conventional semiconductive technology in the solid state and amorphous state, the present process is directed to electrically induced molecular transport in semiconductive media, as distinct from charge transport.

The process of this invention is characterized by a high mobility rate in the separation process which is achieved by tailoring a semiconductive medium for operation at very high voltages and low current density. The voltage applied is preferably in excess of 50 volts/cm and as high as about 25,000 volts/cm. The semiconductive media used in this invention generally comprise several components which are chosen to give a current density in the range of about 0.2 to 100 micro amp/cm$^2$ on filter paper as a substrate. The media should also have a high boiling point. The transport range for this separation process is from about 1 cm/sec to 0.25 cm/min. A further aspect of the process is that an external cooling means is not ordinarily required.

29 Claims, No Drawings

ELECTROMOLECULAR PROPULSION IN SEMICONDUCTIVE MEDIA

THE INVENTION

This invention pertains to a method of exciting a chemical species to achieve mobility for orientating, repositioning and transporting the species and for separation among species achieved by operation at the appropriate conductivity range of the media and especially within the semiconductive range when induced by means of intense electrical fields at or near minimum and optimum current levels. Such systems are characterized by extremely fast molecular motion, or transport, hereinafter called electromolecular propulsion (EMP), as well as by great differentiation or resolution of molecular species. Such resolution is capable of accomplishing very refined analytical separations.

By comparison with conventional techniques, heretofore unobtainable or unique mobilities as well as system versatility can be achieved. This invention provides a method for inducing mobility of molecules previously considered nonmobile due to their nonpolar nature. In the case of polar molecules, such as certain metal derivatives, a greater resolution is obtained than that achieved with conventional conductive or aqueous electrolytes. These, plus additional useful factors favoring this technique, permit exceedingly high resolution separation or purification of different types of molecular species to be efficiently and very rapidly achieved. Suitable detection and/or separation means gives this process an important utility for analytical, purification, and production procedures. It also serves as a research tool for the study, characterization and elucidation of structural and physical-chemical attributes of chemical systems, materials and their interactions.

An aspect of this invention pertains to the preparation of suitable media and systems, within which the semiconductive molecular transport can be reliably accomplished. This can be performed in various media; it being generally convenient to utilize liquids for the mobile phase. The conductivity of the entire system or process is brought within the semi-conductive range by adjusting the conductivity level of the media constituting the mobile phase. Very high voltages may be sustained at low current levels such that the thermoelectric heat buildup ($I^2RT$) nevertheless permits usage of readily available materials and techniques for working systems. In contrast to conventional electrochemical transport methods, in this invention very minute current levels are actually required which correspond to the semi conductive nature of the process. This often precludes the need for employing external heat convective means and permits small working configurations and small power supply size requirements. Another advantage of the process is that at the low heat levels of this invention thermal interference is minimized. The very low current levels which suffice in this invention are near optimum for molecular movement as induced by the attractive-repulsive interaction within the electric field, and, under such conditions, a very intense migratory effect can be induced which is proportional to the voltage potential applied. This migratory effect is characteristic for the molecular nature of the material and may be sharply differentiated from even similarly or related though unidentically structured, molecules. The characteristic mobility of a substance in cm/sec may be used to classify or identify substances. The great degree of molecular resolution or differentiation may be accomplished over the distance of a few inches in a matter of seconds or minutes wherein proportionately less time is required over small distances or by the use of higher voltages. I have discovered that certain low current levels are near optimum for the EMP process and are defined herein as threshold level function dependent upon the molecular nature of the materials involved. The threshold refers to excitation level states in a solvation-adsorption system. The usual observed ranges are $2 \times 10^{-7}$ to $1.6 \times 10^{-5}$ amp/cm 2 for a cellulose substrate. Such threshold levels refer to minimal current requirements for initiating the EMP process and are usually close to the optimum current requirements for a given system. The semiconductive range refers to methods to achieve suitable conductivity at high voltages at the threshold range. The media used are capable of sustaining high voltage electrical fields and are tailored to have a chemically adjusted and/or controlled level of conductivity internal to the mobile phase and in combination with the substrate, by techniques consistent with the various electrical, chemical and operative requirements of the working system.

under such conditions an intense compulsive response with very fast mobility or orientation and high resolution separation of molecular types are readily achieved. Such systems are very convenient and advantageous to operate. Their efficiency is high; heat loss is a minimum, and they are applicable within aqueous, hydrophobic and otherwise non-aqueous media.

This process may be accomplished as a liquid-state semiconductive transport or gaseous state semiconductive transport. Due to its ability to effect molecular transpositions and its use of a mobile phase, it is a semiconductive fluidic process. This distinguishes it from the sessile solid state and amorphous semiconductive systems. By virtue of its effect upon the electromolecular nature of materials through induction by and reaction to suitably intense electrical fields; this process has applications to major classes of known molecular materials including inorganic ions, organic molecules, colloids, and crystalloids. Thus, this process is applicable to inorganic materials such as derived from iron, copper, nickel, cobalt, rare earths, heavy metals, zirconium, and the separation of ionic-solvate species of metal derivatives. It is also applicable to other materials such as proteins, antibiotics, vitamins, antihistamines, amino acids, dyestuffs and blood constituents.

By virtue of the extremely great resolution which can be obtained by application of EMP and the very great speed with which such separations can be achieved, and the various types of systems in which the process can be applied, it offers advantages and applications to various fields and operative procedures, including: analytical chemistry, quality control, clinical chemistry; research; preparative chemistry; physical chemistry; purification; extraction; process control; applied chemistry; and semiconductive technology.

By way of illustration, in preparative chemistry, chemical reactions conducted under suitable EMP conditions can be used to displace reaction equilibria to favor certain yields. It offers a means for selective depletion of equilibrium product from the sphere of the reaction zone, or of contaminants, or byproducts. In extraction, EMP acts as a minimal time consuming process especially when thin walled materials or particulates are involved. In applied chemistry, it is useful where very rapid and/or selective penetrative processing is desired, e.g., in dyeing or destaining fabrics. The dyes or other detectable molecules in a mixture may be individually deposited in a preselected or ordered pattern by control of their EMP response.

Another advantage of the invention is that it permits the separation, characterization, or study of molecular types by virtue of the differential threshold levels. It permits control at different levels under various conditions of pH temperatures, different media, or other internal or external factors. An application of such being a process which is controllable by first operating the system at the lower threshold level to effect the first separation; thereby going on to subsequent levels in order to complete the resolution.

Major operative features for the practice of the invention are:

1. adjusting the operative phase to the semiconductive range to provide operation at/or near molecular threshold levels and maximum or convenient voltage levels capable of being sustained by the system, 2. establishing the optimum current level at or near the molecular threshold level at the given voltage for effective molecular resolution, 3. utilizing those components within the system and arranging the system characteristics such that overall stability, reproducibility, and safety, are attained.

A useful analogy of this phenomena and its relationship to electrochemistry is the comparison of solid state-semiconductive physics with its earlier thermionic electrical technology. Some similarities may be noted from the following characteristics of the EMP process.

1. Power supply wattage (and size) requirements are minimized.

2. Minimal electrothermal losses permit small working dimensions and increased field intensities; this contributes to fast resolution times at low distortion levels.

3. The deteriorating influence upon the system as a result of brute force power requirements, and its attendant heat effects, is eliminated. For example, at higher current densities than those used in this invention the mobility and resolution character of molecular species may be altered.

4. The degree and manner of the electrical utilization is not restricted to the more conventional conductivity modes, such as aqueous electrolyte on transport in liquid phase. Therefore, vast numbers of different types of materials may be acted upon, studied, or utilized in the EMP process. This includes materials and systems whose electrical or ionic contribution would be thought meager from anticipation of their molecular structures. Additionally, a broad range of nonaqueous, hydrophobic, and otherwise nonpolar substances as well as ionic, polar, covalent, aprotic, or other types of conductive substances may be included. This semiconductive fluidic process thereby serves as a new and convenient tool to explore various aspects within these fields, some of which are relatively unknown; as well as to elucidate molecular structure, excitation states, electromolecular interaction and nature of materials.

5. Operation at or near the low threshold levels can be achieved with an overall high electrical propulsive efficiency. These thresholds are characteristic for a material and generally exist at very low power levels. This then defines an operational propulsive efficiency whereby this process is capable of use at power levels just sufficient to effect the molecular species' propulsion, and wherein the electrothermal losses approach negligible values. Actually thermal increments become negligible at very low power levels, especially in a low efficiency electrothermal system. Counteracting factors include evaporative cooling, reservoir heat capacity, thermal convection, and in certain situations dissipation by convective factors such as electroendosmotic streaming. By the controlled operation at increasing threshold levels the molecular species in turn will be induced into propulsion at their appropriate and characteristic level irrespective of other materials which may be present. This provides an additional high resolution technique which is capable of differential molecular discrimination. This discriminatory process is further enhanced by virtue of the propulsion rate also being characteristic for the molecular species involved. This migratory or propulsive rate can be caused to vary substantially by modification of the media.

Appropriate to the mechanism of propulsion threshold it is noted that this behavior determines that point where the molecular attraction or adhesion to the substrate (surface) is counteracted by the total energy input. This is comprised of the external electrical energy input plus what other distribution is due to additional partition functions present. The molecules then being free to migrate or be swept by electricl attraction or other convective factors. The electrical characteristics of the systems show a nonlinearity as the current will gradually rise after the initial application of a given voltage. The preferred systems rapidly stabilize and remain in electrical equilibrium during the separatory process, although the process may be carried out as gradual changes occur in the electrical characteristics. In cases where a lack of stability causes difficulty but the medium is otherwise considered useful, the rate of change in resistance of the system may be reduced by the addition of an external resistance of sufficient magnitude, for example, about equal to or greater than the magnitude of the internal resistance of the system. Alternatively, an active electrical element may be utilized which is capable of sensing the current-voltage or temperature levels within a system and serve to regulate these factors or changes thereby by means of control of the power source. This procedure is also of value as a safety feature.

In practical terms, a key consideration in this process pertains to the use of a relatively nonconductive medium. Various different media and techniques may be used to achieve the requirements of the semiconductive ranges employed. Conduction can be carried out in solids, semisolids, such as gels, as well as in the gaseous phase, aerosols, foams and liquids. Also, combinations of these are practical as are melts, high temperature melts, pseudo crystals (para crystals and mesomorphic materials), ices, slushes, glasses, plastics, fibers, filaments, porous materials and powders. Ion exchange media, permaselective and membrane barriers, dialytic membranes, molecular sieves and specific ion source materials are suitable as supports or barriers. The process may be carried out continuously or by the batch technique.

Many substances are relatively dielectric; of these the nonpolar organics constitute a vast grouping. Some of these exhibit intermediate ranges of conductivity or are susceptible to appropriate adjustment of their conductive nature by addition of relatively small amounts of adjuncts. This may be likened to the process of doping or implantation used with solid-state devices. Other means may include irradiation, polarization interaction, injection of radioactive or charged particulates, photo activation, superposition of AC fields, magnetic fields, counter currents, parametric pumping, centrifugal fields or other energizing means. These energizing fields may be oriented at different angles with respect to the DC field. For example, an AC field superimposed upon the DC field used in this invention may be used to impart additional mobility to chemical species within a medium. Pulsed DC or the superimposition of pulsed DC may also be used. A relatively polar material can be used as the medium, such as aqueous solutions, by limiting the ionic content of the system to achieve the desired conductivity level. Also, suppressive substances can be added to a conductive system; desirable materials being those which exert a suppressive effect beyond the mere dilution effect which their presence contributes to the system. Further, the suppressive effect of nonpolar materials used in comixture with otherwise conducting systems offers a very general and useful approach to the control of conductivity. It is important to note that in regard to all of these techniques other factors may favor certain additional properties and characteristics of the materials employed appropriate for the nature of the application, such as miscibility, compatibility, toxicity, boiling point, melting point, reactivity, cost, removability, dialyzability and osmolality. A high dielectric constant material is often preferred due to its ability to maintain the charges formed in the system (involving solvation or interaction) or charges otherwise acquired or induced upon chemical species. The attainment of a controlled level of conductivity may be further controlled or adjusted by the simultaneous consideration of other system parameters, such as pH, physical state and temperature.

Mixed solvents may be used with the intermediation of a coupling agent, usually of a semipolar cosolvent nature. The term semipolar is used for a material which shows some conductivity, which will increase upon dilution with water (or other similarly polar material), and which will increase upon addition of a soluble ionic salt. Thus, in the present invention the solvation of a strongly ionic material into a nonpolar one by means of a semipolar material will generally produce only a minor conductivity increase; whereas the solution of the ionic material in the semipolar solvent alone may be moderately conducting. In effect, the nonpolar material may be viewed as suppressing the capabilities for moderate conduction to form a three-way system. The three-way system therefore comprises an inert base, a conductivity agent and a semipolar material, such as, respectively, xylene, ammonium bromide and dimethyl formamide. Further, a considerable increase in the amount of the semipolar solvent may only minimally improve the conductivity. The addition of a relatively small volume of a second type of semipolar solvent (a four-way system) can then effect a very substantial conductivity increase of the entire system. Neither cosolvent alone with the nonpolar material, without or including the solvated ionic material will approach the conductivity level so achieved. This technique for augmenting the conductivity of essentially nonpolar materials forms a convenient working basis for the use of substances such as xylene, p-cymene, mineral oil and chlorinated solvents. An illustration, of a four-way system is, xylene, ammonium bromide, dimethyl acetamide and dimethyl formamide.

The above effects also may be applied to systems which are not readily ionizable and the components determined by such factors as dielectric constant and proton donor capability of the solvating molecules. Whereas medium donor capability may give rise to solvated molecules, a high donor capability in a high dielectric system readily tends to preserve the ionic charges so created. Of particular use are media having dielectric constants above 10, which tend to maintain charges formed by proton-donor acceptor exchange.

The media used in this invention are characterized by liquidity at or near room temperature, and sufficiently high boiling points to withstand the process heat. The boiling points are generally above 140° C, and preferably above 165° C. The media need not be capable of dissolving the chemical to which mobility is to be imparted, but solubility is preferable for separation of different molecular species.

This invention is further illustrated by the following examples directed to the separation of chemical species in the indicated media. The apparatus consisted of a high density polyethylene separation cell divided into two 15cc compartments, which is similar in several features to the horizontal suspended strip technique used in low voltage electrochemical processes. The cell was constructed to withstand and provide security from the high voltage fields and conductive leakage of media under such fields and the wide range of strong and corrosive solvent materials used herein. A platinum electrode in each compartment was connected to a DC power souce generally operated at 1.25 ma. The power source was capable of metered operation at variable voltage levels in the ranges of 0–100 ma, 0–1 ma, and 0–10 ma, for threshold studies and operation of the processes described herein. A filter paper wick in each compartment was connected to opposite ends of the filter paper substrate which extended across the top of the cell. The filter paper was 5 cm wide by 10 cm long and except where stated otherwise it was Whatman No. 3. Normally, the voltage drop in this system occurs substantially across the impregnated support, for example from 70 to 90% or more. The cell was enclosed by a transparent cover.

A suitable solvent can be selected from the class of low molecular weight glycols with a minor amount of an additive to increase conductivity. The following solvent systems are useful for relatively nonpolar dyestuffs as well as other soluble organic materials. The solvents listed were used for the separation of mixed chemical species, such as dyes, Mercurochrome, and sodium riboflavin phosphate, at the voltage and current shown. The term "stabilized" is used to indicate that the electrical characteristics reached the indicated values and remained constant for the few minutes (generally 2 to 10 minutes) during which the separation process was completed.

| Ex. | Solvent Formulae | Electrical Characteristic (Stabilized) |
|---|---|---|
| 1 | 0.3 ml. water, 0.2 ml. Sorensen Buffer (pH 7.0), 24.5 ml. propylene glycol. The amount of water in this type of system should preferably not exceed about 2%. | 11 KV/ma |
| 2 | 2.0 ml. dimethyl acetamide, 1.0 ml. phenol, 25.0 ml. propylene glycol. | 8 KV/ma |
| 3 | 2.5 ml. formamide, 22.5 ml. pro- | |

| Ex. | Solvent Formulae | Electrical Characteristic (Stabilized) |
| --- | --- | --- |
|  | pylene glycol. | 5.5 KV/ma |

Example 3 is excellent for dye resolution of the following mixture: saframin O, toluylene red (neutral red) and sodium riboflavin phosphate. This media is also useful for separation of members of the rhodamine dyestuff family.

Unlike conventional ionic-transport processes the mobilization of metal derivatives is not readily achieved, even when the metal derivatives are soluble in the media. However, by adjustment of the media and electrical characteristics in accordance with this invention a very fine resolution is obtained, which illustrates a new mode of operation as described herein. By suitable modification of the above solvent systems, metal ion movement may be made practical, as in the following systems. Examples of suitable metal ions are $Co^{++}$, $Cu^{++}$, $Ni^{++}$ from salts, such as the chlorides and nitrates.

| Ex. | Solvent Formulae | Electrical Characteristic (Stabilized) |
| --- | --- | --- |
| 4 | 10 ml. dimethyl formamide, 15 ml. propylene glycol | 10 KV/ma |
| 5 | 10 ml. dimethyl formamide, 15 ml. propylene glycol, 1 ml. triethanolamine | 8 KV/ma |

Another approach is to use dithizone derivatives of metals such as cobalt, copper and nickel in solvent systems such as (4) and (5) above.

An ester based nonaqueous system is also satisfactory as illustrated below. In place of the cellosolve in the medium, other related compounds can be used, such as hexyl cellosolve, methyl carbitol, cellosolve acetate, and carbitol acetate.

| Ex. | Solvent Formulae | Electrical Characteristic (Stabilized) |
| --- | --- | --- |
| 6 | 4 ml. formamide, 14 ml. cellosolve, 34 ml. dimethyl phthalate | 15 KV/ma |

The following examples show tailoring of the conductivity levels (doping) via nonaqueous salt methods and especially the additional influence of a second semipolar material wherein n-butanol S is a saturated solution of ammonium bromide in n-butanol. This medium is illustrative of a four-way system discussed above, and is useful for the separation of dyes and other compounds soluble therein.

| Ex. | Solvent Formulae | Electrical Characteristic (Stabilized) |
| --- | --- | --- |
| 7 | 5 ml. n-butanol S, 30.5 ml. n-decanol, 2 ml. 1-methyl-2-pyrrolidinone | 14 KV/ma |

The following solvent systems are useful for separation of metal ions and complexes; of the metal complexes, dithizones, nitroso B-napthol, pyrocatechol violet, rhodamine B, 8-hydroxy quinoline, and dibenzoylmethane derivatives were used.

| Ex. | Solvent Formulae | Electrical Characteristic (Stabilized) |
| --- | --- | --- |
| 8 | 30 ml. methoxy ethoxy ethanol + 30 ml. 1,2-propanediol cyclic carbonate + 3 drops nitric acid (1:30 in $H_2O$) | 6.4 KV/1.25 ma |

The medium of Example 8 gave multizone resolution (5 minutes) with rare earth 8-hydroxy quinolinates such as Sc and Eu as well as other metals such as Ni. The heavy metal derivatives of dibenzoylmethane and rhodamine showed good to excellent movement whereas with heavy metal nitrates movement was very sparse and with hafnium (as chloride) not at all. Satisfactory mobility was also obtained for $Co^{+2}$, $Cu^{+2}$, and $Ni^{+2}$ (as chlorides).

In the previous example the nickel chloride gave three zones, with spot coloration of blue and violet. Such reproducible effects demonstrate the very great resolution of the technique. This also points to the formation of a series of metal complexes, such as by proton donor/acceptor exchange, and the ability of the technique to differentiate and resolve them. This unusual capability is evidenced by another situation where not only do multizones appear, but these appear as both (+) or (−) moving entities. Mobility rates of +2 cm/min were achieved with the following systems.

| Ex. | Solvent Formulae | Electrical Characteristic (Stabilized) |
| --- | --- | --- |
| 9 | 15 ml. methoxy ethoxy ethanol + 15 ml. 1,2-propanediol cyclic carbonate + 6 ml. isophorone + 3 drops nitric acid (1:30) | 6.8 KV/ma<br>$Cu^{+2}$ (chloride)<br>3 zones (+ and −)<br>$Fe^{-3}$ (chloride)<br>5–6 zones (+ and −)<br>$Ni^{+2}$ (chloride)<br>3 zones (−)<br>6 min. run |
| 10 | 15 ml. methoxy ethoxy ethanol + 15 ml. 1,2-propanediol cyclic carbonate + 13 ml. ethylene carbonate + 3 drops nitric acid (1:30) | 6 KV/ma<br>$Co^{+2}$ (chloride)<br>2–3 zones (+ and −)<br>$Ni^{+2}$ (chloride)<br>2–3 zones (+ and −)<br>$Cu^{+2}$ (chloride)<br>4–5 zones (+ and −)<br>6 min. run |

The medium of Example 10 also provided excellent mobility for salts of europium, lutetium, thallium and ytterbium. The position, mobility rate, and character of the zones obtained are characteristic for the material within the system under given conditions. Thus, in the following system, nickel and cobalt (as chlorides) gave 1 and 2 zones respectively, whereas the mixture gave 3 zones corresponding to that of the individual metal constituents. Further, the zones had 3 colors with sharply distinguishing pink and blue.

| Ex. | Solvent Formulae | Electrical Characteristic (Stabilized) |
| --- | --- | --- |
| 11 | 21 ml. 1,2-propanediol cyclic | 7.8–7.6 KV/1.25 ma |

| Ex. | Solvent Formulae | Electrical Characteristic (Stabilized) |
|---|---|---|
|  | carbonate + 9 ml. methoxy ethoxy ethanol + 8 ml. γ-Butyrolactone + 3 drops Nitric acid (1:30) | 6 min. run |

Another similar system resolves nickel and cobalt mixtures into pink and blue colored zones. This system is particularly fast with certain nonpolar dyestuffs giving 5 cm/min mobility rates at 7.5 KV levels. Operation at higher voltage levels would increase further the mobility rates:

| Ex. | Solvent Formulae | Electrical Characteristic (Stabilized) |
|---|---|---|
| 12 | 21 ml. 1,2-propanediol cyclic carbonate + 9 ml. methoxy ethoxy ethanol + 12 ml. bis (2-methoxy ethyl) ether + 3 drops nitric acid (1:30) | 8.4–6.6 KV/1.25 ma |

The rare earth groupings as well as hafnium and zirconium represent the most difficult elements for resolution. Further, just as hafnium and zirconium form a particularly close pair, within the rare earths 3 major paired groupings are known. The following systems are useful for the transition and heavy metal categories; including salts of the rare earths and zirconium - hafnium elements, such as those having an atomic number of 21 and greater.

| Ex. | Solvent Formulae | Electrical Characteristic (Stabilized) |
|---|---|---|
| 13 | 15 ml. 1,2-propanediol cyclic carbonate + 15 ml. methoxy ethoxy ethanol + 13 ml. ethylene carbonate + 3 drops nitric acid (1:30) | 9.6–7.2 KV/1.25 ma 3 min. run |

Example 13 was successfully repeated with the medium substantially the same except that in each run the ethylene carbonate was replaced by one of the following: tetrahydrafurfuryl alcohol; isophorone; cellosolve; cyclohexanone; 2-ethylhexyl chloride.

In a system comprising propanediol cyclic carbonate, nitric acid, methoxy methoxy ethanol and tetrahydrafurfuryl alcohol in proportions similar to those above at 500V and 100 μa, the dye saframin O moved readily wherein an orange contaminant remained. This is an example of the separation of components by reaching the threshold level for one compound in a mixture.

Acidification with an inorganic acid is not essential as the following example illustrates.

| Ex. | Solvent Formulae | Electrical Characteristic (Stabilized) |
|---|---|---|
| 14 | 12 ml. 1,2-propylene glycol + 3 ml. dichloro acetic acid + 16 ml. ethoxy ethoxy ethanol | 14 KV/1.5 ma |

Also, media containing bases such as triethanolamine or γ-picoline in place of an acid, have the capability for the separation of metals.

The application of this invention to organic compounds is further illustrated by the following systems used for the separation of sulfa drugs, sulfamerizine, sulfaquanidine and sulfamethazine.

| Ex. | Solvent Formulae | Electrical Characteristic (Stabilized) |
|---|---|---|
| 15 | 20 ml. methoxy ethoxy ethanol + 12 ml. 1-methyl 2-pyrrolidinone + 0.8 ml. dichloracetic acid | 5.8–5.0 KV/1.25 ma 4 min. run |

The latter systems, though found to be slow, was able to yield differential aones with the dyestuff family; rhodamine 5 G, 6 G, and B, as well as a mixture.

The following media gave high resolution of the above dyes in 20–25 seconds and mobility rates in excess of 12 cm/min.

| Ex. | Solvent Formulae | Electrical Characteristic (Stabilized) |
|---|---|---|
| 16 | 24 ml. 1,2-propanediol cyclic carbonate + 12 ml. ethylene diacetate + 6 ml. salicylaldehyde + 3 drops nitric acid (1:30) | 13.2 KV/0.8 ma |

The following two very fast related formulae approach 20 cm/min mobility rates with excellent resolution:

| Ex. | Solvent Formulae | Electrical Characteristic (Stabilized) |
|---|---|---|
| 17 | 24 ml. 1,2-propanediol cyclic carbonate + 12 ml. ethylene diacetate + 6 ml. salicylaldehyde + .4 ml. ammonium bromide (saturated in methoxy ethoxy ethanol) | 14.2 KV/ma |
| 18 | 24 ml. 1, 2-propanediol cyclic carbonate + 12 ml. ethylene diacetate + 6 ml. salicylaldehyde + 2 ml. ammonium bromide (saturated solution methoxy ethoxy ethanol) + 2 ml. tributyl phosphate + 4 drops tetramethyl ammonium hydroxide (about 25% in methyl alcohol) | 13–12.6 KV/ma |
| 19 | 10 ml. tris-chloride (0.14m) + 90 ml | 2 KV/ma |

| Ex. | Solvent Formulae | Electrical Characteristic (Stabilized) |
|---|---|---|
| | water (sucrose to 67%) | |

It is noted that urea or propylene glycol in such systems, in concentrations to several molar, doesn't alter the conductivity, although it may aid the mobility of protein molecules. These substances act as a diluent or suppressant and are useful in water solutions for biochemical separations of substances such as proteins and enzymes. Albumin mobility in such systems can exceed that of glycol soluble dyestuffs, as shown below by the data for migration from the origin.

| Ex. | Solvent Formulae | Electrical Characteristic (Stabilized) |
|---|---|---|
| 20 | 16 ml. tris-chloride (.03m)<br>+ 40 ml. propylene glycol<br>+ 50 ml. glycerin | 6 KV/2 ma<br>Whatman No. 1<br>Albumin 1¼ –<br>1½"<br>Soluble dye ¾"<br>6 min. run |
| 21 | 10 ml. tris-chloride buffer (0.03m)<br>+ 40 ml. propylene glycol<br>+ 50 ml. methylcarbitol | 7.2 KV/2 ma<br>Cellulose acetate paper |

Operation of this process was also carried out by adding a sample to a bed of a gel made from agar, silica, and gelatin. This procedure has been used to separate dyes, proteins and other types of organic compounds The media and electrical characteristics were similar to those described in the preceding examples. Bulk separations have also been carried out in a column with powdered minerals or cellulose supports.

In the preceding formulae, use was made of various types of compounds to perform or provide different important functions. For illustrative purposes, a number of these are selected for arrangement into several categories according to some of their common formulation functions. However, these categories are not rigidly defined limitations for the use of any compounds and some fall equally well across several category boundaries. Thus, dimethyl phthalate is an example of a good suppressant although it also functions as an inert base if used as the base media. Further, it may act to insolubilize or limit mobility of influence other factors, thereby enhancing resolution. Water is useful for a fairly active solvent with moderate proton donor capabilities and high dielectric constant. This latter feature tends to maintain the charges once established. However, water is generally less useful as a major constituent at the higher voltage levels in non-externally cooled systems due to its low boiling point.

Table I

Inert media-base
Characteristic:
minimal conductivity solvent, inert carrier, solution limiter.
p-cymene
mineral oil
n-decanol
1-octanethiol
xylene
Inhibitors (suppressant)
Characteristic:
negative conductivity influence.
tributyl phosphate
dimethyl phthalate
triacetin
2-ethyl hexyl chloride
Neutral media-base
Characteristic:
slight to poor conductivity with tendency for active change in conductivity with dilution solvent, potent solubilizer, coupling agent.
γ-butyrolactone
1,2-propanediol cyclic carbonate
propylene glycol
2-phenoxy ethanol
2-ethyl, 1,3-hexanediol
tetrahydrothiophene 1,1-dioxide
methoxy ethoxy ethanol
Very Active Media
Characteristic:
strong conductivity influence, proton donor solvent action and acidity-alkalinity
Diethyl ethyl phosphonate
n-cyclo-hexyl-2-pyrrolidone
bis (2-methoxy ethyl) ether
Hexa methylene phosphoric triamide
Amino ethyl piperazine
Imino bis propylamine
2,2'-imino diethanol
2-amino ethanol
Triethylene tetramine
triethanolamine
mercaptopropionic acid Conductivity agents
Perchloric acid
dichloracetic acid
formamide
ammonium bromide
pyridazine iodide
nitric acid
mercaptoacetic acid
Active media base
Characteristic:
slight conductivity with tendency to enhance conductivity of neutral media base.
potent solubilizer, solvent
2-chloroacetamide
dimethyl formamide
n,n,-dimethylacetamide
1-methyl-2-pyrrolidone
dimethyl sulfoxide
ethylene cyclic carbonate
2,5-Hexanedione
Modifying agents
isophorone
nitrobenzene
salicylaldehyde
4-hydroxy-4-methyl-2-pentanone
ethylene diacetate
γ-picoline
o-dichlorobenzene Table I-continued mercaptoacetic acid A starting point for developing and choosing a solvent media for particular chemical species is to determine those media which stabilize or are compatible with the species and which exert a good to excellent partition coefficient in a standard chromatographic technique for the species on the substrate to be used at various pH. The conductivity level is then adjusted for use in this process by adding the solvent as a major constituent to a compatible media base system which has a properly adjusted conductivity or, the conductivity of the solvent can be tailored to form a media base system by the use of the types of agents described in Table I. Mobility is normally achieved at about 1.25 ma, which generally exceeds most threshold current levels. Further adjustment may be necessary to initiate or refine the mobility of the species by the adjustment of the composition of the system as indicated above. For example, by the use of complexing agents, modifying agents, similar solvents as determined by chromatographic screening, by pH adjustment and less active substrates (such as teflon).

The compounds listed herein are representative of a much vaster possible grouping of like or related materials useful as solvents, cosolvents, coupling agents with moderate, strong or nil effects on conductivity; many form complexes and metal adducts substantially modifying the effective properties of the metal.

These materials are often used in comixtures to achieve their desired combined properties. Such formulations, aside from their electrical properties, achieve a very broad scope of applicability for different classes of molecular species.

The following list of substances may be considered in three main categories, given below. Other factors to be considered are a larger liquidity range, and dielectric constant, low viscosity, water compatibility and miscibility and strong donor/acceptor influence or neutrality;

1. The major grouping has boiling points at or above 160° C which are liquid at or near room temperature. Generally they have good solvent action.
2. A number of the compounds have boiling points in the 130°–160° C range, or melting slightly above room temperature. These are often used in lesser percentages to modify systems. Also, they often can be liquified with a minor amount of cosolvent.
3. The remainder are modifying agents, whose melting points may be substantially higher and used in solution with other media.

Based upon physical characteristics, chromatographic screening, tests, and the media adjustment techniques described herein, the following compounds are representative of the type useful in this process:

Alcohols
2-aminoethanol 2-ethylaminoethanol
2,3-epoxy-1-propanol ethylene dinitrilo tetraethanol
2,2-iminodiethanol dl-menthol
2-mercaptoethanol
furfuryl alcohol
tetrahydro furfuryl alcohol
2,2'-oxydiethanol
2,2'2''-nitrilotriethanol
1,1'1''-nitrilotri-2propanol
1-phenylethanethiol
2-phenoxyethanol
2,2'-(phenylimino) diethanol
1,3-propane dithiol
thiodiethanol
4-pyridine propanol
2-nitro 1-propanol
2-nitro-1-butanol
2-amino-2-(hydroxymethyl)-1,3-propanediol
geraniol
2-methylamino ethanol
2-methyl-2-nitro-1,3-propane diol
2-(hydroxymethyl)-2-nitro-1,3-propanediol
phenol
aziridine ethanol
hydroxy ethyl piperazine
piperazine ethanol
2-Dimethyl amino-2-methyl-1-propanol
sorbitol
glucose
sucrose
ethylene glycol
propylene glycol
dipropylene glycol polyethylene glycol
thiodiethylene glycol
1-octanethiol
4-hydroxy-4-methyl-2-pentanone 5-hydroxy-2-(hydroxymethyl)-4H-pyran-4one
2-(2-ethoxy ethoxy) ethanol
2-[2-(ethoxy ethoxy) ethoxy] ethanol
2-(2-butoxy ethoxy) ethanol
1-[[[2-(2methoxy-1-methyl-ethoxy)]-1-methyl ethoxy]]-2-propanol
n-butanol
1,3 butane diol
1,4-butane diol
2-(2-butoxy ethoxy) ethanol
2-butoxyethanol
2-(2-methoxy ethoxy) ethanol
2-methoxy ethanol
ethoxy ethanol
3-methoxy-1-butanol
2-butoxy-ethanol
2-ethyl hexane-1,3-diol
t-butanol
iso-amylalcohol
caprylic alcohol
decanol dehydroisophytol
glycerin
dehydrolinalool thioglycerol 3-chloro-1,2 propanediol
2-amino-1-butanol
2-amino-2-ethyl-1,3 propanediol
2-amino-2-methyl-1-propanol
tributyl phosphate
triethyl phosphate
tricresyl phosphate
triphenyl phosphate
tri(2-ethyl hexyl)phosphate
tributoxy ethyl phosphate
o, o, o - triethyl phosphoro thioate
diethyl ethylphosphonate
dibutoxy ethyl sebacate
2-ethyl hexylchloride
bis [2-(2 methoxy ethoxy)

linalool
linalool oxide

Ethers, esters
dibutyl phthalate phenyl acetate dibutyl fumarate
dimethyl phthalate
diethyl phthalate ethyl lactate ethyl malonate
di iso octylazelate di-2-ethyl hexylazelate methyloleate
tri (n-octyl) mellitate tri (n-decyl) mellitate
acetyl tributyl citrate
tributyl citrate
ethylene diacetate tetra hydro furfuryl oleate
tris (chloro ethyl) phosphate
2,2,4-tri methyl-1,3-pentanediol diisobutyrate
di ethoxy ethyl phtholate
methoxy ethyl ricinoleate
glycerol monoacetate
di n-hexyl adipate
glycerol tributyrate
butane diol dicaprylate
ethylene glycol dibenzoate
di ethylene glycol dibenzoate
di propylene glycol dibenzoate
polyethylene glycol (200) dibenzoate
tri ethylene glycol diacetate
bis (diethylene glycol mono ethyl ether) phthalate
bis (2-ethyl hexyl) adipate
1,2-Bis (2-chloroethoxy) ethane
bis (2-chloroethyl) carbonate
bis (2-methoxy ethyl) phtholate
di mercaptodiethyl ether
glycol dimercaptoacetate
di methyl thiodipropionate
tri methylol ethane tri (3-mercapto propionate)
penta erythritol tetra (3-mercaptopropionate)
bis (2-chloro-isopropyl) ether
glycerol triacetate
glycerol tripropionate
1,2/1,3-glycerol diacetate
hexyl acetate ethylmethyl carbamate
hydroxy ethyl acetate
phenyltrimethoxy silane trimethoxy trimethyl mercapto silane
dimethylpoly siloxanes
1,2-bis (2-methoxy ethoxy) ethane 2-(ethoxy ethoxy) ethylacetate
dibenzyl ether

Amides
formamide
N,N-dimethyl formamide

N,N-dimethyl acetamide
2-chloroacetamide
urea
1,1,3,3,-tetra methyl urea
acrylamide
cyanamide
N,N-Bis (2-Cyanoethyl) formamide
2-cyanoacetamide
2-furamide
N-2 hydroxy ethylformamide
N-ethyl p-toluene sulfonamide N-ethyl-o-toluene sulfonamide
N-2-hydroxy ethylacetamide ethyl] ether
bis (2-methoxy ethyl) ether
2-methoxy ethyl acetate
ethoxy ethyl acetate
2-(2-butoxy ethoxy)
ethylacetate
diethylene glycol monomethyl ether
diethylene glycol monoethyl ether
ethylene glycol mono ethyl ether
ethylene glycol mono ethyl ether acetate
ethylene glycol monohexyl ether di ethylene glycol monoethyl ether acetate
di ethylene glycol monomethyl ether
ethyl cyanoacetate
3-acetyl-3-chloropropyl acetate
butyl chloroacetate
butyl lactate
butyl stearate
di tetra hydro furfuryl adipate N-methyl formamide
thioacetamide
picramide
hexamethyl phosphoric triamide
formamidine acetate N-tert-butyl formamide

Lactones, lactams, diones, and carbonates ethylene cyclic carbonate
γ-butyrolactone
2,5-hexanedione
6-hexanolactone
1,2-propanediol cyclic carbonate
oxohexamethylenimine
2,3-butanedione
ethylene trithiocarbonate
propiolactone
2-piperidone
n-butyl carbonate
4,4,4-trifluoro-1,2-thienyl-1,3-butanedione
2,4-pentanedione
dipropyl carbonate
2,4-pentanedione

Nitriles ethylene dinitrilo tetrace-

-continued methane sulfonamide
N-(2-methoxy ethyl) acetamide
N,N'-methylene bis acrylamide
N-Ethyl formamide
Nitriles
hydracrylonitrile
imino diacetonitrile
p-methoxyphenyl acetonitrile
glutaronitrile
succinonitrile
picolino nitrile
nicotinonitrile
benzonitrile
ethylcyanoacetate
4-chloro-3-hydroxybutyronitrile
3,3'-[2,2-Bis(2-cyano ethoxy methyl)-trimethylene dioxy] diproplonitrile
Aldehydes, ketones, thiones, miscellaneous compounds 2'-hydroxyacetophenone
salicylaldehyde
fenchone
4-anisaldehyde
o-chlorobenzaldehyde
isophorone
cyclohexanone
2-piperidone
2-furaldehyde 1-methyl-2-pyrrolidinone 2,6-dimethyl-4-heptanone
p-cymene
o-dichlorobenzene
o-nitrotoluene nitrobenzene
choline
n-ethyl morpholine
2,6-dimethyl morpholine
hexamethylene tetra-amine
2-picoline-1-oxide
tetramethylammoniumhydroxide
tetrabutylammonium hydroxide
tetramethyl guanidine
3-ethyl-4-methylpyridine
5-ethyl-2-methylpyridine hexamethylene imine
tetrahydrothiophene 1,1-dioxide
dimethyl sulfoxide
imino-bis-propylamine
triethylene tetramine
butyraldoxime
2-amino-4-methyl thiazole
n-propyl sulfoxide
n-butyl sulfoxide
alpha picoline
beta picoline
gamma picoline
quinoline 1,2-diazine
aminoethyl piperazine
2-methyl-5-ethyl pyridine
n-hydroxy ethyl piperidine
3-ethyl-4-methyl pyridine
4-ethyl pyridine
2,4-lutidine
2,6-dimethyl pyridine-n-oxide
Lewis bases
p-toluenesulfonic acid trifluoroacetic acid
amino imino methane sulfinic acid
amino ethane thiol sulfuric acid
2-amino ethyl hydrogen sulfate
perchloric acid
sulfamic acid
phosphoric acid
sulfuric acid
nitric acid
Salts betaine hydrochloride tonitrile
pimelonitrile
3,3-thiodipropionitrile
3,3-oxydipropionitrile
phenylacetonitrile
isosafrole
o-methoxy benzaldehyde
tetrahydroionone
pyridazine iodide
decahydronapthalene
diphenyl methane
durene
d-limonene
turpentine
mineral oil
dichlorophenyl trichlorosilane octadecyltrichlorosilane diphenyl methyl chlorosilane
diphenyl dichloro silane epibromohydrin
1,1,2,2-tetrabromoethane
1,2,3,4-tetrahydronapthalene
tetrachloroethane
1,2,4-trichlorobenzene
indene
pyrrolidinone
1-butyl-2-pyrrolidinone
1-cyclohexyl-2-pyrrolidinone
Basic Compounds - and amines, hydroxides, oxides, sulfides, hydrates, alcoholates, heterocyclics Iodine Chloride-Iodine Systems
Sulfur Chloride-Iodine Systems
benzyltrimethylammoniumhydroxide
betaine hydrate
3-methyl piperazine
4-methyl piperidine
4-methyl thiazole
2-methyl thiazole
2-methyl tetrahydro furan
tetrahydrothiazole
1,4 oxathiane
1,2,3-azimidobenzene
2-amino-4-methyl thiazole
5-amino-1,3-bis(2-ethyl hexyl)-5-methyl hydropyrimidine
3,5 lutidine Acidic Media
methane sulfonic acid
dichloroacetic acid
mercaptoacetic acid
3-mercaptopropionic acid
propionic anhydride
lactic acid
2-chloropropionic acid
propionic acid
sulfoacetic acid
trichloroacetic acid
(ethylene dinitrol) tetraacetic acid
trimethylacetic acid
picric acid
camphoric acid
hexanoic acid
picramic acid
cyanuric acid
picrolinic acid
Lewis acids 2,2'2'' nitrilo triethanol hydrochloride
semicarbazide hydrochloride ammonium formate
ammonium thiocyanate
ammonium nitrate ammonium bromide
lithium bromide
lithium iodide
morpholine oleate
lithium nitrate
lithium hydroxide cesium acetate
cesium chloride

| | |
|---|---|
| choline chloride | cesium carbonate |
| hydroxylammonium acetate | cesium salicylate |
| hexadecyltrimethyl ammonium bromide | |
| guanidine nitrate | potassium iodide |
| | poly vinyl benzyl trimethyl ammonium chloride |
| tetrabutyl ammonium iodide | |
| | hydroxylammonium acid sulfate |
| tetra ethylammonium bromide | |
| tetra methyl ammonium bromide | Lewis salts |
| 1,1,1, trimethyl hydrazonium iodide | |
| acetylcholine bromide | |
| acetylcholine iodide | |
| aminoguanidine nitrate | |
| 6-amino-3-indazolinone dihydrochloride | |
| cyanuric chloride | |
| guanidine acetate | |
| guanidine hydrochloride | |
| amino guanidine bicarbonate | |

As part of the methodology which may be used to categorize the materials such as those listed herein they may be titrated with distilled water and their conductivities obtained. The dilution/conductivity curve so obtained indicates the rate of change of conductivity with dilution as well as the diminishing point or plateau levels of conductivity achieved within reasonable dilution means which helps characterize the materials as to the several categories discussed herein, such as very active solvents, active solvents, etc. The following data illustrates the application of this technique (resistances are given in millions of ohms). The very low plateau of resistance at the indicated dilution levels establishes that dichloroacetic acid and mercaptoacetic acid are in the category of very active media. The somewhat higher plateau of ethylene carbonate and 2,5-hexanedione place them in the category of active media. By such a method of convenient rating scale can be established for evaluation of different media. This technique assists in tailoring media to a desired conductivity value by observation of resistance values at different levels of dilution.

to relate the influence of secondary solvents such as the active or very active type (or inert type for suppressant activity) to the conductivity profile. Such effects are variable or characteristic for the diluted agents to which the secondary diluent is added. Further, the conductivity titration curves may be studied with a particular conductivity-valued diluent which may already be an ionized or higher conductivity system. For example, the dilution of hydroxy compounds and ethers with fairly conductive aqueous ammonium nitrate solution and acetic acid may be cited. The comparison was made where both latter systems had equivalent conductivities. Of the compounds 1,3-butane diol, 2,2-methoxy ethoxy ethanol, 2-oxydiethanol bis (2-methoxy ethyl) ether, sorbitol (40% aqueous solution) and sorbitol (57% aqueous solution) by volume, the dilution of the aforementioned aqueous conductive solutions by the latter compounds generally shows a similar decrease in conductivity over the titration range although certain definite curve shapes were derived. Thus, the relative activity and suppressant profile of the various dilutants became evident. With this technique,

| Sample | Initial Resistance, 0.3 ml. | Resistance With .05 ml. Water Added | Resistance With 1 ml. Water Added |
|---|---|---|---|
| dichloroacetic acid | 100 | 0.042 | 0.001 |
| mercaptoacetic acid | 1 | 0.050 | 0.004 |
| ethylene carbonate | 0.2 | 0.20 | 0.065 |
| 2,5-hexanedione | 7 | 2.2 | 0.060 |

Often even partial miscibility with water is sufficient to indicate the range of activity or character to be expected. Further, these studies are extended by titration against materials other than water. Thus, for example dichloroacetic acid, formamide and thiodiethylene glycol were used. These then represent a different solvent miscibility capability and profile. Of these agents, the formamide has a very high dielectric constant and greater conductivity than water, whereas the thiodiethylene glycol's conductivity was in the range of the wate used and also achieved the level of conductivity of the water when a drop of water was added: that is, only slight dilution with the water. The conductivity changes so produced by dilution with non-aqueous materials was further characterized by observing changes in plateau levels so produced by addition of a minor quantity of secondary solvents which may be water. This helps the substantial difference with bis (2- methoxy ethyl)ether is readily evident. Also differences were noted of the effects of aqueous sorbitol at various concentrations, as compared to the non-aqueous materials, upon the ionized ammonium nitrate solution which was, otherwise somewhat less pronounced than upon a dilute acetic acid solution. Further, the various systems may be studied as they effect equilibria characteristics, ionization and/or formation data for the materials of interest and at various pH's. A large compendium or library of data may be prepared for these various possibilities in order to achieve a lessened empirical basis for conditions of system selection for use. As a result of this invention an already established broad table is given of basic solvent systems from which future screening can be made to develop media for use with particular species.

As illustrated by the above examples and the lists of chemicals, the process of this invention comprises separating or mobilizing chemical species which are conveniently on a support such as filter paper in a medium of low conductivity across which a high voltage is impressed. The media-base comprises one or more compounds, for example, inorganic or organic compounds such as glycols, ethers, esters, diones, lactones, amides, nitriles, alcohols and water. An agent may be added to the medium to adjust its conductivity and such agent may be selected from the group consisting of water, acids, bases and salts. The voltage used in the process is within the range of about 50 to 25,000 volts/cm. At very high voltages, and particularly with volatile or gaseous substances, cooling may be required. The preferred range is about 200 to 3,000 volts/cm, and in this range the process can be carried out without external cooling. The conductivity of the medium is preferably adjusted to provide a current density in the range of about from 0.2 to 100 micro amps/sq.cm. based on the area of, for example, filter paper as a substrate. The preferred range is 1.4 to 54 microamps/sq.cm. For bulk work and with external cooling, current densities above 100 micro amps/sq. cm. can be used. The transport medium, after appropriate adjustment of its conductivity, is subjected to a sufficiently high voltage at a low current level (at about the threshold level) to induce separation of the chemical species therein at a rate of about 1 cm/sec. to about 0.25 cm/min. In the above examples, at the conditions indicted, no external cooling was required.

I claim:

1. A process which comprises imparting mobility to a chemical species by providing a semiconductive transport medium which will allow operation at a high voltage and low current density and impressing a voltage with the range of about 50 to 25,000 volts/cm across the medium sufficiently high to produce a current density in the range of about 0.2 to 100 microamp/cm$^2$ and equal to or exceeding the threshold current value for the species in the medium below which value said species remain substantially stationary to induce a high mobility rate for the species.

2. The process of claim 1 wherein the species is on a support member in the medium and the current density applied across the medium is from about 1.4 to 54 micro amp/cm$^2$.

3. The process of claim 1 wherein the medium comprises a neutral media-base, and at least a conductivity or modifying agent and the chemical species is one or more heavy metal compounds.

4. The process of claim 3 wherein said neutral media-base is selected from the group consisting of γ-butyrolactone; 1,2-propanediol cyclic carbonate; propylene glycol; 2-phenoxy ethanol; 2-ethyl, 1,3-hexanediol; tetrahydrothiophene 1,1-dioxide; and methoxy ethoxy ethanol, the conductivity agent is selected from the group consisting of Perchloric acid, dichloracetic acid, formamide, ammonium bromide, pyridazine iodide, nitric acid and mercaptoacetic acid, the modifying agent is selected from the group consisting of isophorone, nitrobenzene, salicylaldehyde, 4-hydroxy-4-methyl-2-pentanone, ethylene diacetate, γ-picoline and o-dichlorobenzene, and wherein the conductivity of the neutral media-base is adjusted by at least one of said agents to provide a current density in the range of about 1.4 to 54 microamps/sq. cm. at a voltage of about 200 to 3000 volts/cm.

5. The process of claim 1 wherein the medium comprises a solvent for said species, and said solvent has a dielectric constant of at least 10.

6. The process of claim 1 where the threshold level is reached for one species and said current is maintained below the threshold for a second species, thereby separating said species.

7. The process of claim 1 wherein said species are selected from a group consisting of metal compounds and organic compounds, and said medium comprises aprotic subtances or inorganic substances.

8. The process of claim 1 wherein the transport medium exhibits non-linear electrical characteristics upon application of said voltage.

9. The method of separating chemical species which comprises mixing said species with a semiconductive medium and applying a high voltage and a low current density across said medium wherein said semiconductive medium comprises a base solvent for said species and an additive to provide a current density of about 1.4 to 54 microamps/sq. cm. across the medium at an applied voltage of about 200 to 3000 volts/cm.

10. The method of separating a mixture of substantially nonpolar dyes which comprises mixing said dyes with a semiconductive medium on a substrate and applying a high voltage at a low current density across said substrate.

11. The method of claim 10 wherein said semiconductive medium comprises a low molecular weight glycol and an additive to increase conductivity to provide a current density of about 1.4 to 54 micramps/sq. cm. across the support at an applied voltage of about 200 to 3000 volts/cm., and said substrate is a cellulose strip.

12. The method of separating chemical species which comprises mixing said species with a semiconductive medium and applying a high voltage and a low current density across said medium wherein said semiconductive medium comprises as a major constituent a substantially nonconductive, nonpolar solvent for said species and at least one additive to provide a current density of about 0.2 to 100 microamps/sq. cm. across the medium at an applied voltage of about 50 to 25,000 volts/cm., said solvent is selected from those which are compatible with said species and which exhibit a suitable partition coefficient for the species in a standard chromatographic technique, and said medium has a high dielectric content above 10 to maintain charges formed by proton donor/acceptor interactions between the medium and the species.

13. In the method of separating chemical species on a substrate in a fluid medium the improvement which comprises
   providing a solvent medium which is substantially non-conductive and non-polar
   adjusting the conductivity level of the solvent with an additive to form a semi-conductive medium to provide a current density of about 0.2 to 100 microamps/sq. cm. across the medium at an applied voltage of about 50 to 25,000 volts/cm. and wherein the semi-conductive medium is characterized by a high dielectric content above 10 to maintain charges formed by proton donor/acceptor interactions, and a boiling point above 140°C for the medium
   applying said chemical species on said support and dissolving said chemical species in said medium and applying a voltage of 50 to 25,000 volts/cm. across the medium at a low current density to overcome the residual binding energy for the species in the medium to induce a mobility for the chemical species between about 1 cm./sec. and 0.25 cm./min. without the application of external cooling means.

14. A process which comprises imparting mobility to a non-polar chemical species by providing an electrically nonlinear, semiconductive transport medium a residual binding energy existing between said species and medium tending to maintain said species in generally fixed relationship to said medium, said medium being of dielectric constant greater than 10 and providing charged transfer interaction capability without chemical reaction being of the proton donor/acceptor type with charge deficient molecular species, and adapted to allow operation at a high voltage and low current density, and impressing a voltage within the range of about 50 to 25,000 volts/cm across the medium sufficiently high to produce a current density in the range of about 0.2 to 100 microamp/cm$^2$ and equal to or exceeding the threshold current value to overcome the residual binding energy for the species in the medium to induce a high mobility rate for the species.

15. The process of claim 14 wherein the species is on a support member in the medium.

16. The process of claim 15 wherein said support member is selected from the group consisting of a cellulose substrate, a gel, a membrane and porous materials.

17. The process of claim 15 wherein said voltage is from about 200 to 3,000 volts/cm. across the medium.

18. The process of claim 17 in which no external cooling means is used.

19. The process of claim 14 wherein the voltage is raised to a sufficiently high value at a low current density consonant with the threshold level to induce a transport range of the chemical species between about 1 cm/sec. and 0.25 cm/min.

20. The process of claim 14 wherein more than one species is added to the medium and said species are separated by applying said voltage across the medium.

21. The process of claim 14 wherein the medium is substantially nonaqueous.

22. The process of claim 14 wherein said medium comprises a member selected from the group consisting of a glycol, ether, ester, amide, aldehyde, ketone, dione, lactone and alcohol and a conductivity modifier.

23. The process of claim 22 wherein said modifier is present in a minor amount and is selected from the groups consisting of iodine, water, acids, bases and salts.

24. The process of claim 14 wherein the medium comprises an inert media-base, at least one active media base and a conductivity agent.

25. The process of claim 24 wherein said inert media-base is selected from the group consisting of p-cymene, mineral oil, n-decanol, 1-octanethiol and xylene, said active media-base is selected from the group consisting of 2-chloroacetamide, dimethyl formamide n,n,-dimethylacetamide, 1-methyl-2-pyrrolidone, dimethyl sulfoxide, ethylene cyclic carbonate and 2,5-hexanedione, and said conductivity agent is selected from the group consisting of perchloric acid, dichloracetic acid, formamide, ammonium bromide, pyridazine iodide, nitric acid and mercaptoacetic acid.

26. The process of claim 14 wherein the medium comprises an active base, at least one conductivity agent and a suppressant.

27. The process of claim 26 wherein said active base is selected from the group consisting of 2-chloroacetamide, dimethyl formamide, n,n,-dimethylacetamide, 1-methyl-2-pyrrolidone, dimethyl sulfoxide, ethylene cyclic carbonate and 2,5-hexanedione, said conductivity agent is selected from the group consisting of perchloric acid, dichloracetic acid, formamide, ammonium bromide, pyridazine iodide, nitric acid and mercaptoacetic acid, and said suppressant is selected from the group consisting of tributyl phosphate, dimethyl phthalate, triacetin and 2-ethyl hexyl chloride.

28. The process of claim 14 wherein said chemical species comprises a protein, and said medium comprises water and a conductivity suppressant.

29. The process of claim 14 wherein said media has a boiling point above 140°C.

* * * * *

UNITED STATES PATENT AND TRADEMARK OFFICE
CERTIFICATE OF CORRECTION

PATENT NO. : 3,984,298
DATED : October 5, 1976
INVENTOR(S) : Norman Haber

It is certified that error appears in the above–identified patent and that said Letters Patent are hereby corrected as shown below:

Col. 2, line 24 "under" should be --Under--.

Col. 8, line 43, delete "$Fe^{-3}$" and substitute --$Fe^{+3}$--.

Col. 10, line 35, delete "aones" and substitute --zones--.

Col. 19, line 61, delete "wate" and substitute --water--.

Delete Table I, from column 11, line 34 to column 13, line 5, and substitute the following:

UNITED STATES PATENT AND TRADEMARK OFFICE
CERTIFICATE OF CORRECTION

PATENT NO. : 3,984,298

DATED : October 5, 1976

INVENTOR(S) : Norman Haber

It is certified that error appears in the above-identified patent and that said Letters Patent are hereby corrected as shown below:

Table I

Inert media-base
Characteristic:
minimal conductivity
solvent, inert carrier
solution limiter.
p-cymene
mineral oil
n-decanol
1-octanethiol
xylene

Inhibitors (suppressant)
Characteristic:
negative conductivity
influence.
tributyl phosphate
dimethyl phthalate
triacetin
2-ethyl hexyl chloride

Neutral media-base
Characteristic:
slight to poor conductivity
with tendency for active
change in conductivity with
dilution solvent, potent
solubilizer, coupling agent.
$\gamma$-butyrolactone
1,2-propanediol cyclic carbonate
propylene glycol
2-phenoxy ethanol
2-ethyl, 1,3-hexanediol
tetrahydrothiophene 1, 1-dioxide
methoxy ethoxy ethanol

Very Active Media
Characteristic:
strong conductivity influence, proton donor
solvent action and acidity-alkalinity.
Diethyl ethyl phosphonate
n-cyclo-hexyl-2-pyrrolidone
bis (2-methoxy ethyl) ether
Hexa methylene phosphoric triamide
Amino ethyl piperazine
Imino bis propylamine
2,2'-imino diethanol
2-amino ethanol
Triethylene tetramine

Very Active Media (cont'd)
triethanolamine
mercaptopropionic acid
mercaptoacetic acid

Conductivity agents
Perchloric acid
dichloracetic acid
formamide
ammonium bromide
pyridazine iodide
nitric acid
mercaptoacetic acid

Active media base
Characteristic:
slight conductivity with tendency
to enhance conductivity of neutral
media base.
potent solubilizer, solvent
2-chloroacetamide
dimethyl formamide
n,n-dimethylacetamide
1-methyl-2-pyrrolidone
dimethyl sulfoxide
ethylene cyclic carbonate
2,5-Hexanedione

Modifying agents
Isophorone
nitrobenzene
salicylaldehyde
4-hydroxy-4-methyl-2-pentanone
ethylene diacetate
$\gamma$-picoline
o-dichlorobenzene

UNITED STATES PATENT AND TRADEMARK OFFICE
CERTIFICATE OF CORRECTION

PATENT NO. : 3,984,298
DATED : October 5, 1976
INVENTOR(S) : Norman Haber

It is certified that error appears in the above—identified patent and that said Letters Patent are hereby corrected as shown below:

--Delete tables starting at cols. 13-14 at line 33 through cols. 19-20 at line 19, and substitute the following:

Alcohols
2-aminoethanol
2-ethylaminoethanol
2,3-epoxy-1-propanol
ethylene dinitrilo tetraethanol
2,2-iminodiethanol
dl-menthol
2-mercaptoethanol
furfuryl alcohol
tetrahydro fufuryl alcohol
2,2'-oxydiethanol
2,2' 2"-nitrilotriethanol
1,1' 1"-nitrilotri-2 propanol
1-phenylethanethiol
2-phenoxyethanol
2,2'-(phenylimino) diethanol
1,3-propane dithiol
thiodiethanol
4-pyridine propanol
2-nitro 1-propanol
2-nitro-1-butanol
2-amino-2-(hydroxymethyl)-1,3-propanediol
geraniol
2-methylamino ethanol
2-methyl-2-nitro-1,3-propanediol
2-(hydroxymethyl)-2-nitro-1,3-propanediol
phenol
aziridine ethanol
hydroxy ethyl piperazine
piperazine ethanol
5-hydroxy-2-(hydroxymethyl)-4H-pyran-4-one
2-(2-ethoxy ethoxy) ethanol
2-[2-(ethoxy ethoxy) ethoxy] ethanol
2-(2-butoxy ethoxy) ethanol
1-[[[2-(2-methoxy-1-methyl-ethoxy)]-1-methyl ethoxy]]-2-propanol
n-butanol
1,3 butane diol
1,4-butane diol
2-(2-butoxy ethoxy) ethanol
2-butoxyethanol
2-(2-methoxy ethoxy) ethanol
2-methoxy ethanol
ethoxy ethanol Alcohols (cont'd)
3-methoxy-1-butanol
2-butoxy-ethanol
2-ethyl hexane-1,3-diol
t-butanol
iso-amylalcohol
caprylic alcohol
decanol
dehydroisophytol
glycerin
dehydrolinalool
thioglycerol
3-chloro-1,2 propanediol
2-amino-1-butanol
2-amino-2-ethyl-1,3 propanediol
2-amino-2-methyl-1-propanol
2-Dimethyl amino-2-methyl-1-propanol
sorbitol
glucose
sucrose
ethylene glycol
propylene glycol
dipropylene glycol
polyethylene glycol
thiodiethylene glycol
1-octanethiol
4-hydroxy-4-methyl-2-pentanone
linalool
linalool oxide Ethers, esters
dibutyl phthalate
phenyl acetate
dibutyl fumarate
dimethyl phthalate
diethyl phthalate
ethyl lactate
ethyl malonate
di iso octylazelate
di-2-ethyl hexylazelate
methyloleate
tri(n-octyl) mellitate
tri(n-decyl) mellitate
acetyl tributyl citrate
tributyl citrate
ethylene diacetate
tributyl phosphate
triethyl phosphate
tricresyl phosphate
triphenyl phosphate

UNITED STATES PATENT AND TRADEMARK OFFICE
CERTIFICATE OF CORRECTION

PATENT NO. : 3,984,298

DATED : October 5, 1976

INVENTOR(S) : Norman Haber

It is certified that error appears in the above-identified patent and that said Letters Patent are hereby corrected as shown below:

Ethers, esters (cont'd)
tri(2-ethyl hexyl) phosphate
tributoxy ethyl phosphate
o,o,o-triethyl phosphoro
   thioate
diethyl ethylphosphonate
dibutoxy ethyl sebacate
2-ethyl hexylchloride
bis[2-(2 methoxy ethoxy)
   ethyl] ether
bis(2-methoxy ethyl) ether
2-methoxy ethyl acetate
ethoxy ethyl acetate
2-(2-butoxy ethoxy)
   ethylacetate
diethylene glycol monomethyl
   ether
diethylene glycol monoethyl
   ether
ethylene glycol mono ethyl
   ether
ethylene glycol mono ethyl
   ether acetate
ethylene glycol monohexyl
   ether
di ethylene glycol monoethyl
   ether acetate
di ethylene glycol monomethyl
   ether
ethyl cyanoacetate
3-acetyl-3-chloropropyl
   acetate
butyl chloroacetate
butyl lactate
butyl stearate
di tetra hydro fufuryl adipate
tetra hydro furfuryl oleate
tris (chloro ethyl) phosphate
2,2,4-tri methyl-1,3-pentanediol
   diisobutyrate
di ethoxy ethyl phthalate
methoxy ethyl ricinoleate
glycerol monoacetate
di n-hexyl adipate
glycerol tributyrate
butane diol dicaprylate
ethylene glycol dibenzoate
·di ethylene glycol dibenzoate
di propylene glycol dibenzoate
polyethylene glycol (200)dibenzoate Ethers, esters (cont'd)
tri ethylene glycol diacetate
bis(diethylene glycol mono ethyl ether)
   phthalate
bis (2-ethyl hexyl) adipate
1,2-Bis(2-chloroethoxy) ethane
bis(2-chloroethyl)carbonate
bis(2-methoxy ethyl) phthalate
di mercaptodiethyl ether
glycol dimercaptoacetate
di methyl thiodipropionate
tri methylol ethane tri(3-mercapto
   propionate)
penta erythritol tetra (3-mercaptopropionate)
bis(2-chloro-isopropyl) ether
glycerol triacetate
glycerol tripropionate
1,2/1,3-glycerol diacetate
hexyl acetate
ethylmethyl carbamate
hydroxy ethyl acetate
phenyltrimethoxy silane
trimethoxy trimethyl mercapto
   silane
dimethylpoly siloxanes
1,2-bis(2-methoxy ethoxy) ethane
2-(ethoxy ethoxy) ethylacetate
dibenzyl ether Amides
formamide
N,N-dimethyl formamide
N,N-dimethyl acetamide
2-chloroacetamide
urea
1,1,3,3-tetra methyl urea
acrylamide
cyanamide
N,N-Bis (2-Cyanoethyl)
   formamide
2-cyanoacetamide
2-furamide
N-2 hydroxy ethylformamide
N-ethyl p-toluene sulfonamide
N-ethyl-o-toluene sulfonamide
N-2-hydroxy ethylacetamide
methane sulfonamide
N-(2-methoxy ethyl) acetamide
N,N'-methylene bis acrylamide
N-Ethyl formamide

UNITED STATES PATENT AND TRADEMARK OFFICE
CERTIFICATE OF CORRECTION

PATENT NO. : 3,984,298
DATED : October 5, 1976
INVENTOR(S) : Norman Haber

It is certified that error appears in the above—identified patent and that said Letters Patent are hereby corrected as shown below:

Amides (cont'd)
N-methyl formamide
thioacetamide
picramide
hexamethyl phosphoric triamide
formamidine acetate
N-tert-butyl formamide Lactones, lactams, diones, and carbonates
ethylene cyclic carbonate
$\gamma$-butyrolactone
2,5-hexanedione
6-hexanolactone
1,2-propanediol cyclic carbonate
oxohexamethylenimine
2,3-butanedione
ethylene trithiocarbonate
propiolactone
2-piperidone
n-butyl carbonate
4,4,4-trifluoro-1,2-thienyl-1,3-butanedione
2,4-pentanedione
dipropyl carbonate
2,4-pentanedione Nitriles
ethylene dinitrilo tetracetonitrile
pimelonitrile
3,3-thiodipropionitrile
3,3-oxydipropionitrile
phenylacetonitrile
hydracrylonitrile
imino diacetonitrile
p-methoxyphenyl acetonitrile
glutaronitrile
succinonitrile
picolino nitrile
nicotinonitrile
benzonitrile
ethylcyanoacetate
4-chloro-3-hydroxybutyronitrile
3,3'-[2,2Bis(2-cyano ethoxy methyl)-trimethylene dixoy] diproplonitrile Aldehydes, ketones, thiones, miscellaneous compounds
2'-hydroxyacetophenone
salicylaldehyde
fenchone
4-anisaldehyde
o-chlorobenzaldehyde
isophorone
cyclohexanone
2-piperidone
2-furaldehyde
1-methyl-2-pyrrolidinone
2,6-dimethyl-4-heptanone
p-cymene
o-dichlorobenzene
o-nitrotoluene
nitrobenzene
isosafrole
o-methoxy benzaldehyde
tetrahydroionone
pyridazine iodide
decahydronapthalene
diphenyl methane
durene
d-limonene
turpentine
mineral oil
dichlorophenyl trichlorosilane
octadecyltrichlorosilane
diphenyl methyl chlorosilane
diphenyl dichloro silane
epibromohydrin
1,1,2,2-tetrabromoethane
1,2,3,4-tetrahydronapthalene
tetrachloroethane
1,2,4-trichlorobenzene
indene
pyrrolidinone
1-butyl-2-pyrrolidinone
1-cyclohexyl-2-pyrrolidinone Basic Compounds and amines, hydroxides, oxides, sulfides, hydrates, alcoholates, heterocyclics
Iodine Chloride-Iodine Systems
Sulfur Chloride-Iodine Systems
benzyltrimethylammoniumhydroxide
betaine hydrate

UNITED STATES PATENT AND TRADEMARK OFFICE
CERTIFICATE OF CORRECTION

PATENT NO. : 3,984,298
DATED : October 5, 1976
INVENTOR(S) : Norman Haber

It is certified that error appears in the above-identified patent and that said Letters Patent are hereby corrected as shown below:

Basic Compounds and amines, hydroxides, oxides, sulfides, hydrates, alcoholates, heterocyclics
choline
n-ethyl morpholine
2,6-dimethyl morpholine
hexamethylene tetra-amine
2-picoline-1-oxide
tetramethylammoniumhydroxide
tetrabutylammonium hydroxide
tetramethyl guanidine
3-ethyl-4-methylpyridine
5-ethyl-2-methylpyridine
hexamethylene imine
tetrahydrothiophene 1,1-dioxide
dimethyl sulfoxide
imino-bis-propylamine
triethylene tetramine
butyraldoxime
2-amino-4-methyl thiazole
n-propyl sulfoxide
n-butyl sulfoxide
alpha picoline
beta picoline
gamma picoline
quinoline
1,2-diazine
aminoethyl piperazine
2-methyl-5-ethyl-pyridine
n-hydroxy ethyl piperidine
3-ethyl-4-methyl pyridine
4-ethyl pyridine
2,4-lutidine
2,6-dimethyl pyridine-n-oxide
Lewis bases
3-methyl piperazine
4-methyl piperidine
4-methyl thiazole
2-methyl thiazole
2-methyl tetrahydro furan
tetrahydrothiazole
1,4 oxathiane
1,2,3-azimidobenzene
2-amino-4-methyl thiazole
5-amino-1,3-bis(2-ethyl hexyl)-5-methyl hydropyrimidine
3,5 lutidine Acidic Media
methane sulfonic acid
dichloroacetic acid
mercaptoacetic acid
3-mercaptopropionic acid
propionic anhydride
lactic acid
2-chloropropionic acid
propionic acid
sulfoacetic acid
trichloroacetic acid
(ethylene dinitrol) tetra acetic acid
trimethylacetic acid
picric acid
camphoric acid
hexanoic acid
picramic acid
cyanuric acid
picrolinic acid
Lewis acids
p-toluenesulfonic acid
trifluoroacetic acid
amino imino methane sulfinic acid
amino ethane thiol sulfuric acid
2-amino ethyl hydrogen sulfate
perchloric acid.
sulfamic acid
phosphoric acid
sulfuric acid
nitric acid Salts
betaine hydrochloride
choline chloride
hydroxylammonium acetate
hexadecyltrimethyl ammonium bromide
guanidine nitrate
tetrabutyl ammonium iodide
tetra ethylammonium bromide
tetra methyl ammonium bromide
1,1,1 trimethyl hydrazonium iodide
acetylcholine bromide
acetylcholine iodide
aminoguanidine nitrate

UNITED STATES PATENT AND TRADEMARK OFFICE
CERTIFICATE OF CORRECTION

PATENT NO. : 3,984,298
DATED : October 5, 1976
INVENTOR(S) : Norman Haber

It is certified that error appears in the above-identified patent and that said Letters Patent are hereby corrected as shown below:

Salts (cont'd)
6-amino-3-indazolinone dihydrochloride
cyanuric chloride
guanidine acetate
guanidine hydrochloride
amino guanidine bicarbonate
2,2' 2" nitrilo triethanol hydrochloride
semicarbazide hydrochloride
ammonium formate
ammonium thiocyanate
ammonium nitrate
ammonium bromide
lithium bromide
lithium iodide
morpholine oleate
lithium nitrate
lithium hydroxide
cesium acetate
cesium chloride
cesium carbonate
cesium salicylate
potassium iodide
poly vinyl benzyl trimethyl ammonium chloride
hydroxylammonium acid sulfate
Lewis salts Signed and Sealed this Twenty-eighth Day of December 1976

[SEAL]

Attest:

RUTH C. MASON
*Attesting Officer*

C. MARSHALL DANN
*Commissioner of Patents and Trademarks*